US00PP18561P2

(12) United States Plant Patent

Shibamichi

(10) Patent No.: US PP18,561 P2

(45) Date of Patent: Mar. 4, 2008

(54) *ACER PALMATUM* PLANT NAMED 'GARNET TOWER'

(50) Latin Name: ***Acer Palmatum* var. *dissectum***
Varietal Denomination: Garnet Tower

(75) Inventor: Akira Shibamichi, Kawaguchi (JP)

(73) Assignee: ItSaul Plants, LLC, Atlanta, GA (US)

( * ) Notice: Subject to any disclaimer, the term of this patent is extended or adjusted under 35 U.S.C. 154(b) by 4 days.

(21) Appl. No.: 11/519,651

(22) Filed: Sep. 12, 2006

(51) Int. Cl.
*A01H 5/00* (2006.01)

(52) U.S. Cl. ..... Plt./224

(58) Field of Classification Search ..... Plt./224
See application file for complete search history.

*Primary Examiner*—Kent Bell
*Assistant Examiner*—June Hwu
(74) *Attorney, Agent, or Firm*—Penny J Aguirre

(57) ABSTRACT

A new cultivar of *Acer palmatum* var. *dissectum,* 'Garnet Tower', characterized by its unique upright plant habit, it's deeply dissected and purple colored foliage, its purple stems, and its ability to be readily graphed on *Acer palmatum* rootstock.

2 Drawing Sheets

Botanical classification: *Acer Palmatum* var. *dissectum.*
Variety denomination: 'Garnet Tower'.

BACKGROUND OF THE INVENTION

The present invention relates to a new and distinct cultivar of *Acer palmatum* var. *dissectum,* and will be referred to hereafter by its cultivar name, 'Garnet Tower'. 'Garnet Tower' is a deciduous tree grown for use as a landscape plant.

'Garnet Tower' was selected as unique primarily for its upright growth habit combined with its red foliage. The new *Acer* was selected in the summer of 1999 in Kurume City, Kyushu, Japan as a naturally occurring branch sport of *Acer palmatum* var. *dissectum* 'Garnet' (not patented).

Asexual reproduction of the new cultivar was first accomplished by grafting onto *Acer palmatum* rootstock in March 2000 in Kurume City, Kyushu, Japan. The characteristics of this cultivar have been determined to be stable and are reproduced true to type in successive generations.

SUMMARY OF THE INVENTION

The following traits have been repeatedly observed and represent the characteristics of the new cultivar as observed for ten years in Kurume City, Japan and for three years in a test garden in Atlanta, Ga. These attributes in combination distinguish 'Garnet Tower' as a unique cultivar of *Acer palmatum* var. *dissectum.*

1. 'Garnet Tower' has a unique upright growth habit. The species, *Acer palmatum* var. *dissectum* have branches with a weeping habit.
2. The palmate foliage is dissected and primarily purple in color.
3. The stem color of 'Garnet Tower' is green with a overlay of purple that intensifies with sun exposure and in fall.
4. 'Garnet Tower' is readily grafted onto *Acer palmatum* rootstock.

In comparison to the parent plant, *Acer palmatum* var. *dissectum* 'Garnet', 'Garnet Tower' was an upright habit, whereas 'Garnet' with similar foliage coloration, has a weeping plant habit as is typical for species. 'Garnet Tower' can also be compared to *Acer palmatum* var. *dissectum* 'Lionheart' (not patented). 'Lionheart' is similar to 'Garnet Tower' in that it has red foliage and an upright habit, however unlike 'Garnet Tower', the habit becomes weeping as the tree matures.

BRIEF DESCRIPTION OF THE DRAWING

The accompanying colored photographs of 'Garnet Tower' illustrate the overall appearance and distinct characteristics of the new *Acer palmatum* var. *dissectum.*

Figure 1:
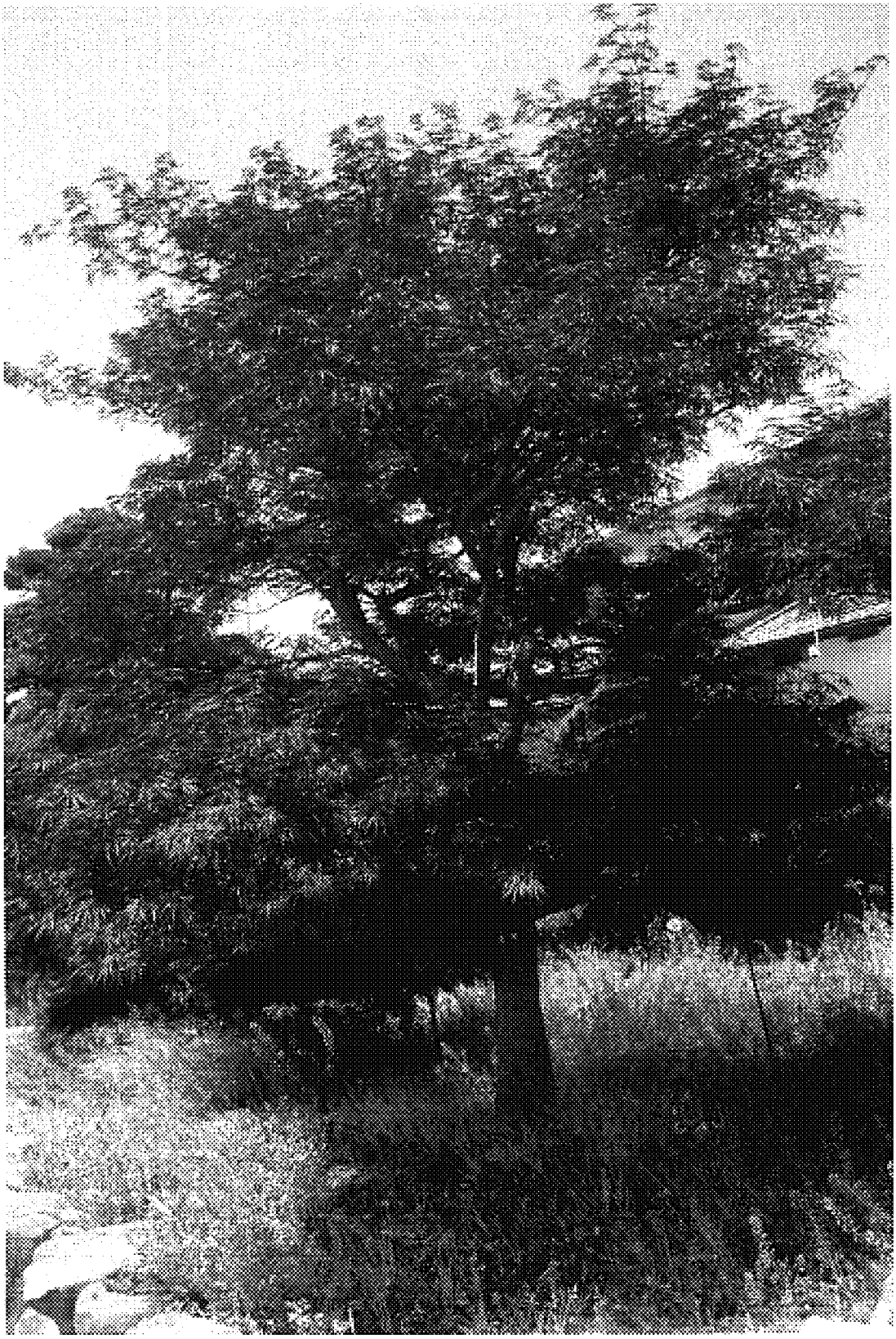
FIG. 1 was taken of a ten year-old plant of 'Garnet Tower' as grown in Kurume City, Japan and provides a view of the plant habit of a mature plant.
Figure 2:
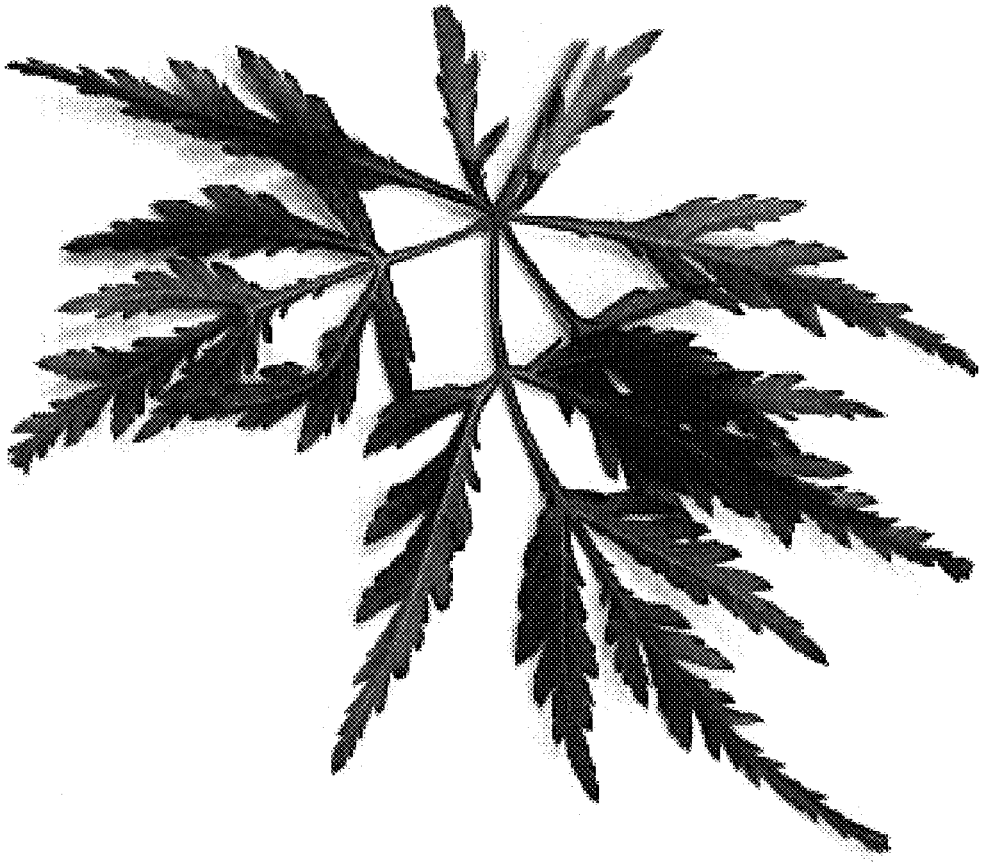
FIG. 2 provides a close-up view of the upper surface of a leaf.

The colors in the photographs are as close as possible with the digital photography techniques available, the color values cited in the detailed botanical description accurately describe the colors of the new *Acer palmatum* var. *dissectum.*

DETAILED BOTANICAL DESCRIPTION

The following is a detailed description of the new cultivar as grown outdoors for ten years in Kurume City, Japan and in a trial garden in Atlanta, Ga. for three years. The phenotype of the new cultivar may with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Botanical classification.*—'Garnet Tower' is a cultivar of *Acer palmatum* var. *dissectum.*

*Parentage.*—Naturally occurring branch sport mutation of *Acer palmatum* var. *dissectum* 'Garnet'.

*Plant habit.*—Deciduous tree with an upright habit.

*Height and spread.*—Reaches about 4 m (13 ft) in height and about 2.5 to 3 in width (8 to 10 ft.) in ten years.

*Cold hardiness.*—U.S.D.A. Zones 5.

*Diseases and pests.*—No susceptibility or resistance to diseases or pests known to affect *Acer palmatum* var. *dissectum* has been observed for 'Garnet Tower'.

*Root description.*—Fibrous, freely branched.

Growth and propagation:

*Propagation.*—Grafted into *Acer palmatum* root stock.

*Time required for graft development.*—About 4 weeks to develop to a 36-cell tree pot.

*Growth rate.*—Moderately vigorous.

Stem description:

*Shape.*—Round to slightly oval.

*Stem color.*—Main trunk and secondary branches (bark) 197B, foliaged branches; growth underlay color of 144A (yellow-green) with overlay of N77A (purple), purple coloration is most intense with sun exposed branches and in fall.

*Stem diameter.*—Main trunk; up to about 25 cm in diameter at base, secondary branches; up to about 8 cm in diameter, and tertiary branches (with foliage) average of 5 mm in diameter.

*Stem surface.*—Glabrous.

*Internode length.*—About 3 to 5 cm.

Foliage description:

*Leaf shape.*—Roughly ovate in overall outline, palmately lobed, lobes lanceolate in overall shape.

*Leaf division.*—Simple.

*Leaf base.*—Hastate.

*Leaf apex.*—Acute, very narrow at apex.

*Leaf fragrance.*—None.

*Leaf venation.*—Primary are palmate, secondary odd-pinnate, not conspicuous, 146C on upper and lower surface of young leaves, color matching leaf color on fall leaves.

*Leaf margins.*—Palmate with 7 lobes, lobes are Pinnatisect with deeply incised to dissected margins.

*Leaf arrangement.*—Opposite.

*Leaf aspect.*—Held upright on petioles held horizontal or up to about a 45° angle from branch.

*Leaf attachment.*—Petiolate.

*Leaf surface.*—Glabrous on upper and lower surface, lower surface slightly shiny.

*Leaf size.*—Up to about 9 cm in length and width, leaflets; center lobe up to about 8 cm in length and 2.5 cm in width, side lobes up to about 6.5 cm in length and 2 cm in width, lower lobes up to about 2 cm in length and 0.5 cm in width.

*Leaf color.*—Newly expanded and mature leaves: upper surface; 139A with overtones of N186C and narrow margins of N186C, lower surface; 137A with narrow margin of 186C, fall foliage: upper surface 147A heavily overlaid with N186B (greyed-purple), lower surface 17A with shading of N186B to 186C (greyed-purple).

*Petioles.*—About 3 to 4 cm in length and 1 mm in width, held horizontal to about a 45° angle upward from branch. color is 184A with areas of 144A at leaf attachment and branch attachment, attachment region is expanded and 3 mm in diameter.

Inflorescence description: Flowering has not been observed under the conditions tested.

I claim:

1. A new and distinct cultivar of *Acer palmatum* var. *dissectum* plant named 'Garnet Tower' as herein illustrated and described.

* * * * *